United States Patent
Moghadamfalahi et al.

(10) Patent No.: US 10,573,335 B2
(45) Date of Patent: Feb. 25, 2020

(54) METHODS, SYSTEMS AND APPARATUSES FOR INNER VOICE RECOVERY FROM NEURAL ACTIVATION RELATING TO SUB-VOCALIZATION

(71) Applicant: HONEYWELL INTERNATIONAL INC., Morris Plains, NJ (US)

(72) Inventors: Mohammad Moghadamfalahi, Plymouth, MN (US); Umut Orhan, Kirkland, WA (US); Michael Dillard, St. Louis Park, MN (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/926,408

(22) Filed: Mar. 20, 2018

(65) Prior Publication Data
US 2019/0295566 A1    Sep. 26, 2019

(51) Int. Cl.
*G10L 25/48* (2013.01)
*G10L 25/30* (2013.01)
*G06F 3/01* (2006.01)

(52) U.S. Cl.
CPC .............. *G10L 25/48* (2013.01); *G06F 3/015* (2013.01); *G10L 25/30* (2013.01)

(58) Field of Classification Search
CPC .......... G10L 25/48; G10L 25/30; G06F 3/015
See application file for complete search history.

(56) References Cited

U.S. PATENT DOCUMENTS

| | | | |
|---|---|---|---|
| 9,451,883 B2* | 9/2016 | Gallant | A61B 5/0042 |
| 2008/0103769 A1* | 5/2008 | Schultz | G10L 15/24 |
| | | | 704/235 |
| 2013/0184588 A1* | 7/2013 | Palti | A61B 8/06 |
| | | | 600/454 |
| 2015/0297106 A1* | 10/2015 | Pasley | A61B 5/0476 |
| | | | 600/378 |
| 2015/0338917 A1 | 11/2015 | Steiner et al. | |

(Continued)

OTHER PUBLICATIONS

Pengfei Sun and Jun Qin, Neural Networks based EEG-Speech Models, Mar. 31, 2017, all (Year: 2017).*

(Continued)

*Primary Examiner* — Sonia L Gay
(74) *Attorney, Agent, or Firm* — Lorenz & Kopf, LLP

(57) ABSTRACT

Methods, systems and apparatuses are provided to perform a continuous-to-continuous mapping of neural signal data received from one or more body sensors connected to an user wherein the one or more body sensors monitors at least neural activities of the user of a sub-vocalized voice at a sensory level and sends the neural signal data to a processor. The processor receives the neural signal data in an iterative closed loop to train the processor and to generate a sufficiently large data set in the neural signal domain to link to a produced voice domain. The processor constructs a common feature space which associates the neural signal domain with the produced voice domain wherein the common feature space implicitly extracts features related to audio communications for linking neural signal domain data to the produced voice data without requiring any prior feature classification of the received neural signal data.

6 Claims, 5 Drawing Sheets

(56) References Cited

U.S. PATENT DOCUMENTS

2015/0380009 A1   12/2015   Chang et al.

OTHER PUBLICATIONS

Kosmyna, N. et al.; Adding Human Learning in Brain-Computer Interfaces (BCIs): Towards a Practical Control Modality; ACM Transactions on Computer-Human Interaction, vol. 22, No. 3, Article 12, Publication date: May 2015.

Wang, K. et al.; Simulation Experiment of BCI Based on Imagined Speech EEG Decoding; May 22, 2017.

Duarte Mendes De Almeida; Using Brain-Computer Interface to understand and decode neural processes associated with imagined speech.

* cited by examiner

METHODS, SYSTEMS AND APPARATUSES FOR INNER VOICE RECOVERY FROM NEURAL ACTIVATION RELATING TO SUB-VOCALIZATION

TECHNICAL FIELD

The present invention generally relates to sub-vocalization and more particularly to methods, systems, and apparatuses for inner voice monitoring and recovery by a continuous mapping of neural activations of user sub-vocalizations.

BACKGROUND

Sub-vocalization processes, in general, relate to the domain of silent speech (SSP) and synthetic telepathy and limited advancements to date have occurred both in invasive and non-invasive domains of SSP. SSP can be produced in a variety of ways: (I) by talking by moving the speech articulators of a person but without producing any audible sound where the signals may be captured using Electromyography (EMG) sensors placed around the neck and mouth; (II) by imagery speech where a person imagines the word to be produced and (III) by talking in the mind without moving any speech articulators and without making any audible sound (i.e., sub-vocalization).

Neural Computer Interfaces (NCI) with the brain are communication and/or control systems that allow real time interaction for SSP between the human brain and external devices, without the need for vocalization. Using electroencephalography (EEG), NCIs for connecting and monitoring motor cortex functions of the brain, SSP detections may be enabled with sufficient signal-to-noise ratios generated from neural activities of the signals of the brain than other past invasive techniques used in signal generation that in addition, only met with limited success. EEG NCIs may allow for reinforcing the learning process of persons while maintaining minimally an invasive set of characteristics. Thus speech-like NCIs based on patterns of EEG recordings, is feasible. Through machine learning algorithms and pattern recognition, NCIs may be able to translate brain activity, predict a user's intents and convert them into commands which control external devices.

Sub-vocalization applications can eliminate deficiencies found in speech recognition applications particularly in noisy environments. However, sub-vocalization applications have applicability in wide domain areas that are not applicable to speech recognition applications, particularly when communications are needed not to be revealed. For example, sub-vocalization applications rather than voice recognition application are suited for use in silent communications in crowded environments, for confidential communications between parties, for sharing private information in public spaces while maintaining privacy; for communicating with parties without providing notice of communicating or revealing the communications to other third parties, for transmitting classified communications between parties or government entities etc. In addition, current voice recognition systems also use noise cancelation to try to achieve high accuracy in speech recognition in a noisy environment; and to reduce the environmental variations which cause noise in the speech signal. However, the use of noise cancelation is relatively ineffective to combat high levels of environmental noise distortions as well as variations in the level themselves that occur.

Hence, it is desirable to address these inadequacies raised in speech recognition in the communications that occur in various domains of internal and external communications by inner voice sub-vocalization methods, systems and apparatuses and to improve an overall NCI performance to allow for improved accuracy of sub-vocalization speech communications. The present disclosure addresses at least this need.

BRIEF SUMMARY

Methods, Systems and Apparatuses are provided for sub-vocalization using ANN for nonlinear modeling and learning through iterations without requiring prior classification of recorded neural data.

In an exemplary embodiment, a method for sub-vocalization is provided. The method includes: performing, by a processor, a continuous-to-continuous mapping of neural signal data received from one or more body sensors connected to an user wherein the one or more body sensors monitors at least neural activities of the user of a sub-vocalized voice at a sensory level and sends the neural signal data to the processor; receiving, by the processor, the neural signal data in an iterative closed loop for training the processor wherein the training enables generating a sufficiently large data set in the neural signal domain from the neural signal data to link to a produced voice domain; and constructing a common feature space, by the processor, which associates the neural signal domain with the produced voice domain for producing audio communications wherein the common feature space implicitly extracts features related to audio communications using the sufficiently large data set by the common feature space for linking neural signal domain data to the produced voice data without requiring any prior feature classification of the received neural signal data.

The method further includes: modeling by artificial neural networks (ANN) the continuous-to-continuous mapping of neural signal data received from the one or more body sensors connected to the user. The method includes: learning, by the processor, by iterations of the closed loop training of the processor a mapping of the common feature space for a set of common neural signal domain activity. The method includes: learning by a set of ANN based algorithms of the ANN while simultaneously modeling the common feature space. The method includes: mapping by a first function the neural signal domain, and targeting by a second function the mapping of the first function to the produced voice domain to reproduce the subvocalized voice. The method includes: using a f(x) by the first function for mapping to the common feature space, and using an inverse $G^{-1}(x)$ by the second function for targeting to the produced voice. The method includes: monitoring, by the one or more body sensors, neural domain data of sub-vocalized voice of a set of neural signals at least comprising: electroencephalography (EEG), electromyography (EMG), Electroencephalography (EGG) and Functional Near-Infrared Spectroscopy (FNIRS) signals. The mapping performed is agnostic as to an intent of the user or monitoring of neural activities.

In yet another embodiment, a sub-vocalization system of imagined speech is provided. The sub-vocalization system includes: a plurality of body sensors; and a processor to perform a continuous-to-continuous mapping of neural signal data received from one or more body sensors from the plurality of body sensors connected to an user wherein the one or more body sensors monitors at least neural activities of the user of a sub-vocalized voice at a sensory level and sends the neural signal data to the processor, the processor configured to: process, a set of neural signal data received from the one or more body sensors, in an iterative closed loop for training the processor wherein the training generates a sufficiently large data set in the neural signal domain from the neural signal data to link to a produced voice domain; and construct, a common feature space, which associates the neural signal domain with the produced voice domain to produce audio communications wherein the common feature space implicitly extracts features related to audio communications, using the sufficiently large data set, by the common feature space to link neural signal domain data to the produced voice data without requiring any prior feature classification of the received neural signal data.

The system further includes: an artificial neural network (ANN) to model the continuous-to-continuous mapping of neural signal data received from the one or more body sensors connected to the user. The system further includes: the processor configured to: perform a data learning by iterations of the closed loop training of the processor of a mapping of the common feature space for a set of common neural signal domain activity.

The system further includes: the processor configured to: perform a data learning by a set of ANN based algorithms of the ANN while simultaneously performing a data modeling of the common feature space. The system further includes: the processor configured to: perform a first function to map the neural signal domain, and perform a second function to target the map of the first function to the produced voice domain to reproduce the subvocalized voice. The system further includes: the processor configured to: perform a f(x) for use by the first function to map to the common feature space, and perform an inverse G−1(x) for use by the second function for targeting to the produced voice. The system further includes: the set of body sensors configured to: monitor a set of a plurality of neural signals monitored for recording neural domain data of sub-vocalized voice, the set of neural signals at least comprises: electroencephalography (EEG), electromyography (EMG), Electroencephalography (EGG) and Functional Near-Infrared Spectroscopy (FNIRS) signals. The mapping by the processor is agnostic as to an intent of the user or type of neural activities.

In yet another embodiment, an apparatus for sub-vocalization system for imagined speech recognition is provided. The apparatus includes: a processing module to perform a continuous-to-continuous mapping of neural signal data received from one or more body sensors connected to an user wherein one or more of the body sensors monitors at least neural activities of the user of sub-vocalized voice at a sensory level and sends the neural signal data to the processor; and a set of neural signal data, from the one or more body sensors, received by the processing module in an iterative closed loop for training the processing module wherein the training generates a sufficiently large data set in the neural signal domain from the neural signal data to link to a produced voice domain.

The apparatus further includes: the processing module configured to: construct a common feature space which associates the neural signal domain with the produced voice domain to produce speech communications. The common feature space implicitly extracts features related to speech communications, using the sufficiently large data set, by the common feature space to link neural signal domain data to the produced voice data without requiring any prior feature classification of the received neural signal data. The produced speech communications are produced without any natural language processing (NPL) by the processing module.

This summary is provided to describe select concepts in a simplified form that are further described in the Detailed Description.

This summary is not intended to identify key or essential features of the claimed subject matter, nor is it intended to be used as an aid in determining the scope of the claimed subject matter.

Furthermore, other desirable features and characteristics of the system and method will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

Figure 1:
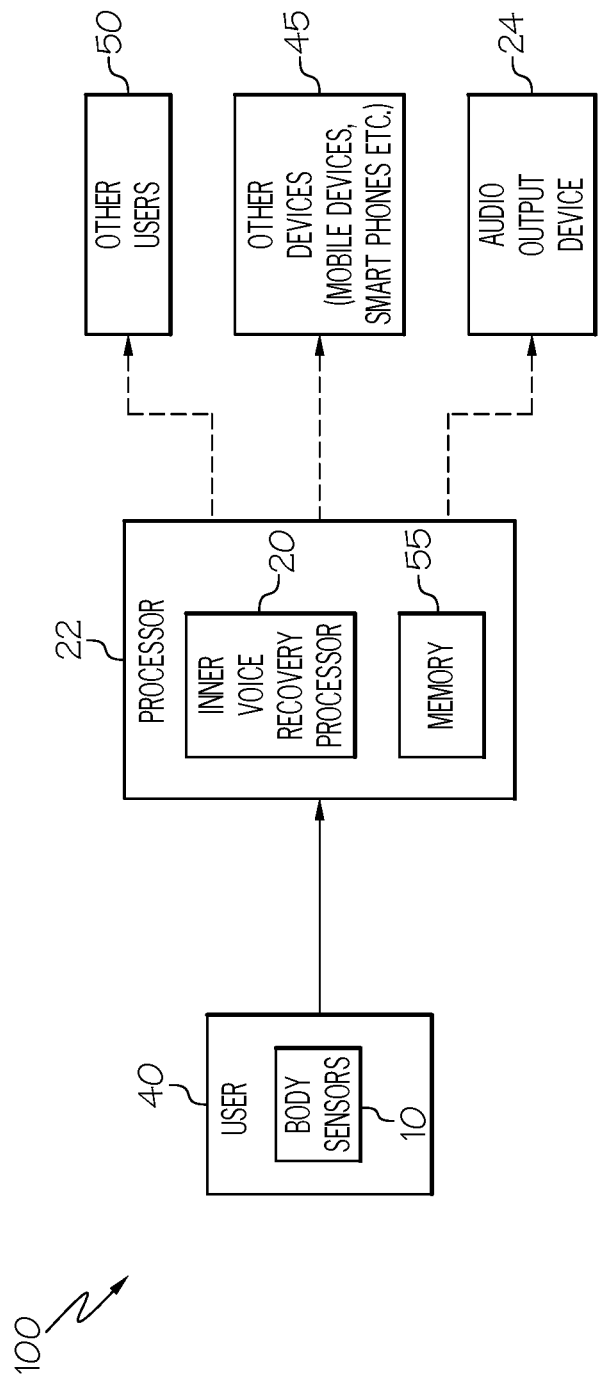
FIG. 1 is a block diagram of a sub-vocalization speech recovery system in accordance with the exemplary embodiments described herein.

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All the embodiments described herein are exemplary embodiments provided to enable persons skilled in the art to make or use the invention and not to limit the scope of the invention that is defined by the claims. Furthermore, there is no intention to be bound by any expressed or implied theory presented in the preceding technical field, background, brief summary, or the following detailed description.

It is contemplated that are wide variety of signal types may be recorded by use of bodily worn sensors including Electroencephalography (EEG), Electromyography (EMG), Electroencephalography (EGG) and Functional Near-Infrared Spectroscopy (FNIRS) for neural domain data sets for sub-vocalization. References to EEG types of signals should not be construed as limiting in any way but encompass other signal types that may be recorded in place of or conjunction with EEG signals recorded for sub-vocalization methods and systems.

Sub-vocalization may be construed broadly and non-limiting to encompass imagined speech, inner voice, internal speech, speech articulated with or without minuscule movements in the larynx and other muscles involved in the articulation, silent speech, internal monologue, self-talk, verbal streams of consciousness etc.

In addition, sub-vocalization methods and systems described are not restricted to neural activities. That is, inner voice recovery from neural activations relating to sub-vocalization of externally not visible muscle (EMG) or electrical vocal cord activities (Electroglottography-EGG) are also feasible sources of signals to utilize, both individually or in conjunction with EEG or any other neural signal sources.

The signal recording of EEG is difficult for a number of reasons: 1) EEG recording suffer from different types of artifacts, 2) EEG is a very noisy signal (low signal to noise ratio), 3) when recording EEG signals, sensors record often almost the same signals (because EGG signals are mathematically hard to distinguish from each other), 4) EEG signal depends on several unknown parameters (ex. user specific, task specific, other variables), 5) when capturing EEG signals intrusions may occur such as non-brain signals, head motions, muscle movements, and some other unexpected stimulus, and 6) large connections of neurons generating electrical signals are involved in different activities making it difficult to quantify a particular subset of signals related to an action.

It is feasible for a user to wear an electroencephalography (EEG) cap on the head and, with some training, could enable a user to stop and start his brain's alpha waves to compose messages. The initial steps towards realization of this goal occurred to a limited extent in the field of biomedical engineering with the aim of developing interventions for people who suffer from severe muscle and speech impairments. DARPA, IARPA, and the military have shown interest and invested in brain computer interface (BCI) technology because the level of secrecy and privacy that such system can offer in a military, aviation, or intelligent operational setup. For that matter, not only do military/intelligent applications benefit but also other tasks which need silence due to a required concentration, privacy and/or secrecy may benefit from direct translation of brain activity to actions or interpretable information. Smart environments such as smart houses, workplaces, or transportation settings could also use BCIs in offering further safety, luxury, and physiological control in daily life, for instance in home control. Also a cooperation between Internet of Things (IoT) and BCI technologies is feasible. For example, it may deemed possible to enable a fast and reliable communication BCI which ensures privacy by enabling phone calls without producing any sounds in a working environment or send voice massages in public places without being heard.

Speech recognition has drawbacks. That is, speech recognition technologies have been integrated into such areas but the success of the integration of these speech recognition technologies has been limited because requirements of speech recognition technologies for success are dependent on achieving a high accuracy in speech recognition as well as overcoming a plethora of unique challenges such as dialect, accents Some of the current speech recognition systems use speaker dependent speech engines which depend both on knowledge of a particular speaker's voice characteristics and receiving voiced communications with high levels of clarity to discern the voice characteristics in order to achieve the required accuracy levels. While requiring sufficient but different training like sub-vocalization system, speech engines have the added burden of having to recognize the voiced speech characteristics of the user during implementation. However, such speaker dependent voice recognition systems may not always feasible for use in particular environments. Sub-vocalization systems, on the other hand, are agnostic to external noise obtrusions and disturbances therefore are feasible for implementation in environments with external conditions that speech recognition systems could not perform.

Speech recognition is the process of converting a speech signal into a sequence of words. Speech recognition may also be referred to as Automatic Speech Recognition ("ASR") or Speech-to-Text ("STT") while inner voice recovery is the recovery of silent or sub-vocalization speech. The use of speech recognition has become ubiquitous and is used in many aspects of a daily life. For example, use may be found in automotive systems or environment in which users are busy with their hands, home automation (e.g., voice command recognition systems), speech-to-text processing (e.g., word processors or emails), and personal assistants on mobile phones (e.g., APPLE SIRI® on iOS, MICROSOFT CORTANA® on WINDOW®'s Phone, GOOGLE® NOW on ANDROID®). Similarly, it is envisioned that sub-vocalization voice recovery will be as ubiquitous in the future.

Speech processing in the brain is composed of two parts in communication (the latter part is the focus of inner voice recovery): the sensory part, i.e. language input, and the motor part, i.e. language output. While the former requires sensory organs, such as ears and eyes, the latter mainly involves vocalization and its control (which also requires sensory, e.g. auditory, feedback). It is also possible to identify two main pathways for communication. One consists of hearing and speaking, while the other involves reading and speaking. In the first case the sequence the reception in the primary auditory area of the sound signals that encode words and the interpretation of the words in Wernicke's area, the main cortical area for language comprehension. The determination of the thoughts and words to be spoken in Wernicke's area FIG. 1 illustrates a sub-vocalization speech recovery system in accordance with the exemplary embodiments described herein. FIG. 1 is a functional block diagram of a sub-vocalization system 100 in accordance with an exemplary embodiment. The sub-vocalization system 100 includes at least one processor 22 and at least one audio output device 24, which is operatively coupled to processor 22. During the operation of the sub-vocalization system 100, the processor 22 drives audio output device 24 to produce voiced sub-vocalizations sensed by the body sensors 10. The processor 22 includes an inner voice recovery processor 20 and may be used to provide the functions of the inner voice recovery processor 20. The inner voice recovery processor 20 may convert received sub-vocalization speech transmissions to text as well as perform appending of text and concatenating of text messages with the converted speech transmissions. The inner voice recovery processor 20 does not perform natural language processing ("NLP") of received sensed data from the user 40 but map continuously using a flexible neural network framework, the electrical signals sensed or detected movements of the user into neural domains for targeting to a linked voice or audio domain. The inner voice recovery processor 20 may perform or assist the processor 22 in performing functions related to contextual interpretations and aggregations of received broadcasted and transmitted voice transmissions.

The memory 55 can be external to and operatively coupled to processor 22, or instead integrated into processer 22. In one embodiment, a processor and memory of the processer 22 reside in an Application Specific Integrated Circuit ("ASIC"). Memory 55 may store data, such as various software or firmware, supporting operation of processer 22 and other components. Also, it is contemplated that the sub-vocalization system may be used in an Internet of Things environment may be connected or interconnected with other devices 45, other users 50 and the like.

Continuing with FIG. 1, inputs of body sensors 10 are received of a user from the body sensors 10 while worn by the user which generate electrical signals including EEG, EMG, EGG, FNIRS, which are further processed to convert the generated neural electrical signals into audio signals. That is the inner voice recovery processor 20 can determine speech without vocalization by the user via receiving neural input data or silent data from the body sensors 10. For example, neurological signals in the brain can be detected by electrodes coupled to the speech motor cortex of the brain of a user which are used to detect the neural electrical signals of sub-vocalization speech sounds. The patterns of the sub-vocalization signals of speech sounds can be decoded and correlated to speech patterns to determine particular speech. In an exemplary embodiment, the inner voice recovery processor 20 may, for example, target the EEG, EMG, EGG, FNIRS in the audio signal domain for linking to a produced voice for enabling voice/audio communications with other users 50, other devices 45 etc.

In an exemplary embodiment, an inner voice recovery processor 20 receives the electrical signals and divides the electrical signals into three signal spaces or representations of an audio signal space, a physiological signal space and a common space, where the audio signal space and the physiological signal space can be mapped onto the common space. That is, by a long training process of iteratively mapping the electrical signals to the common space, coarticulation of speech from the sub-vocalizations of the brain can be determined without having to classify the electrical signals. The iterative mapping inherently by repetition enables the classifying corpus of the electrical signals. That is, the inner voice recovery processor 20 by using artificial neural networks ("ANN") modeling that learns from examples through iterations without requiring a prior knowledge of the relationships of neural signal data of the electrical signals, the inner voice recover processor 20 is capable of coping with the uncertainness, noisy data, and non-linear relationships of the neural signal data received from the body sensors 10. In alternative embodiments, modeling of the neural signal data may be modeled on an Encoder-Decoder architecture with recurrent neural networks and neural machine translation (NMT).

In an exemplary embodiment, the inner voice recovery module 20 may be employed with a speech recognition processor 25 to enhance accuracy of speech recognition applications. For example, current voice recognition systems use noise cancelation to try to achieve high accuracy in speech recognition in a noisy environment; and to reduce the environmental variations which cause noise in the speech signal. For sub-vocalization applications, the noise level of the external environment has at best limited effect and therefore it is feasible to use results of language processing from sub-vocalization applications to enhance, corroborate, or assist voice recognition applications with accuracy of natural language processing.

Figure 2:
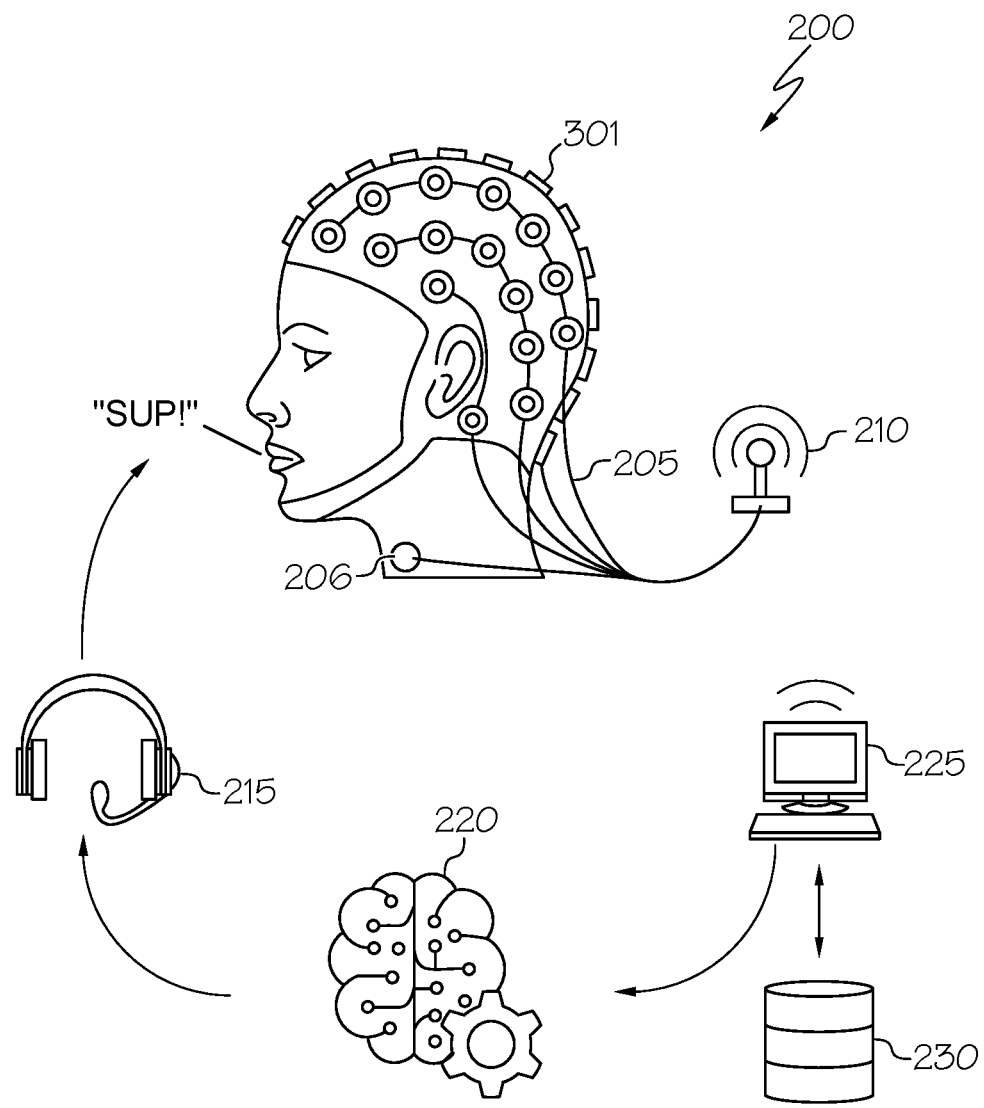
FIG. 2 is a diagram of a sub-vocalization speech recovery system in accordance with the exemplary embodiments described herein.

FIG. 2 illustrates a diagram of a sub-vocalization speech recovery system in accordance with the exemplary embodiments. With a reference to FIG. 2, a BCI as in the inner voice recovery system 200 can be considered a closed loop or cyclical flow of neural signal data interactions between a user and the processing system. Generally, the user interacts with such the processing system and the processing system gives feedback about its decision state after the interaction. The BCI loop may be composed of various elements (in order): the signal acquisition process; the signal processing step, in which signals are processed and prepared; the feature extraction phase, in which to identify and extract salient features from the signal; and a classification stage (omitted in the inner voice recovery system 200), in which the features are matched to the classifier model to identify one of the phenomena it was trained to capture.

The use of a BCI system is to assign a brain signal of a fixed duration (an epoch; e.g., 1s) at time t, to a class Cli from a set of N classes Cl that correspond to a set of brain activity states BSi that need to be recognized. A machine-learning classifier C may be used trained to recognize the desired states BSi through a set of training examples T(Cli) for each class Cli. A training example is a signal epoch of the same duration as St that was recorded when the user was in the desired state BSi corresponding to the class Cli. This is called the training or calibration phase.

With continuing reference to FIG. 2, the inner voice recovery system 200 includes electrodes 205 located in the vicinity of the brain area to detect neural signals of brain activity of the user 201, and any physiological sensor 206 to capture neural activity related to larynx or nearby facial muscles, e.g. electroglottography or Electromyography signal. For example, the user may subvocalize speech and neural activity would occur as a result of the user thoughts. This activity is recovered by the electrodes 205 from electrical activity of the neurons in the brain may instance be indicative of a pattern to be associated with user commands. That is, the electrodes 205 may transmit the recovered signals of neural activity to transmit via a transmitter to the EEG output 210 to a processor device 225 with processing capabilities to perform a continuous-to-continuous mapping of the received sensory/motor level of neural activity in various data structures.

The neural activity recordings are captured in the data repository 230 after processing from the processing device 225. The feedback mechanism via auditory instructions to the user 201 by the headphones 215 lessens any lack of association between EEG output 210 and cortical processes of the brain 220 which may occur due to the inherently low signal-to-noise ratio of EEG signals. That is, EEG data may be obscured by erroneous electrical signals from non-cerebral origins. Such erroneous electrical signals or artifacts may be relatively to the size of the amplitude of the cortical signals generated. The sources of such artifacts may stem from electromyographic (muscle activation) signals, or electrocardiographic (cardiac) signals. In addition, a factor inhibiting the classification of EEG data for the task of sub-vocalization speech recognition is an inherently poor signal-to-noise ratio (SNR). Even minute electromyographic (or muscle) movements, such as eye blinking, facial expressions, and neck motions may induce comparatively dominant signals that overwhelm and obscure the signals produced from the brain. Additionally, the brain also produces many signals that are irrelevant to sub-vocalization speech recognition.

Classifying high-dimensional EEG data given the wide range and abnormalities in the EEG data can prove difficult, because it is not often clear how sub-vocalization speech will manifest itself within the EEG data generated. Further, the brain is a dynamic system with non-periodic signals, it is necessary to model it as a dynamic system. Further, as a result of the extremely low signal-to-noise ratio in EEG signals, effective machine learning algorithms need large data sets to isolate the valuable components from the noise.

Such large data sets are cumbersome to produce due to the need for specialized hardware equipment and deliberate human attention to collect valid labeled training samples. Additionally, when EEG (or any other measurements related to neural activity) data, is collected, it is not guaranteed to be consistent or complete. As a result of the inconsistent nature of human focus and attention span, it is also difficult to assure that data samples are accurately labeled. Because the nature of human attention span is unpredictable and volatile, it cannot be guaranteed that a subject is actually thinking clearly about the specified word or idea, nor can an accurate measure of the users level of focus or level of distraction during the data collection process be assessed.

In order to extract valid feature information from high dimensional EEG signals, it is necessary to use machine learning and pattern recognition algorithms. Machine learning techniques can already be used to recognize a small set of thought-based commands within EEG signals. Supervised learning algorithm are applicable for usage for EEG feature extraction purposes of an Artificial Neural Network (ANN). ANNs can mimic the human brain because the ANN has structural parallels with biological neural networks, ANNs may be used for learning to recognize patterns in EEG signals.

In an exemplary embodiment, EEG signals for the electrodes maybe sampled at in the vicinity of 256 Hz for 1 second following at pre-determined periods. The signals may also be hardware-filtered to a frequency in the vicinity of a range of 0.1 Hz to 50 Hz. Users may imagine speaking two or more syllables and then subvocalize them, while their electrical brainwave activity is recorded by EEG and their larynx neural activity is recorded by EGG or EMG. These syllables, during sub-vocalization phase, may contain no semantic meaning so that a mapping would be performed on the sub-vocalization speech instead of the semantic contribution to sub-vocalization speech production. The user may for example be instructed to silently voice a given syllable at a certain rhythm, both of which may be provided via audio cues of the headphones. The headphone also can playback the reproduced audio to provide a closed-loop system for the user to direct her/his neural activity to produce the desired sound. In other words, the user may listen to the produced sounds to apply a measure of correctness. For example, such a playback via the headphone can be analogized to a user hearing his/her own voice inside her head.

Next, the received data is unstructured, and by using various software applications, the unstructured data may be mapped to a common feature space (that has been prior empirically derived) using any number of mapping application and schema generators that provides sufficient clustering capabilities for large data sets. Feedback is provided to the user from the processor device 225 to the user by playing back the reproduced audio to headphones 215 worn by the user. The sensory and sensory-motor level identification/mapping is performed between neural activity and audio. This mapping is a nonlinear regression from the neural activity signal to the audio signal domain either through a third common feature space or directly. The reproduced audio playback to the user closes the loop of learning process in which both processor device 225 and the user will learn by the continuous and iterative interaction.

In this interaction, processor device 225 will query the user with specific sentences of sounds. During the subvocalizing, the processor device 225 will provide real time feedback to the user for him/her to shift his/her brain activity to achieve the best performance by the processor device 225. In addition, supervised data collections will happen episodically and after each collection procedure the processor device 225 will update the data mapping to incorporate any non-invasively recorded electrical activity of the brain or any other measured activity related to larynx strings or facial muscles, related to sub-vocalization activities. This is because, the EEG signal related to neural activation during auditory sensation is correlated with the envelope of the sound. Hence, there exists a relationship between the envelope of the intended voice to produce and neural activation at the sensory/motor level. Further, tapping into the sensory or sensory-motor components may allow for any extraction of the semantic meanings when combined with NLP.

Figure 3:
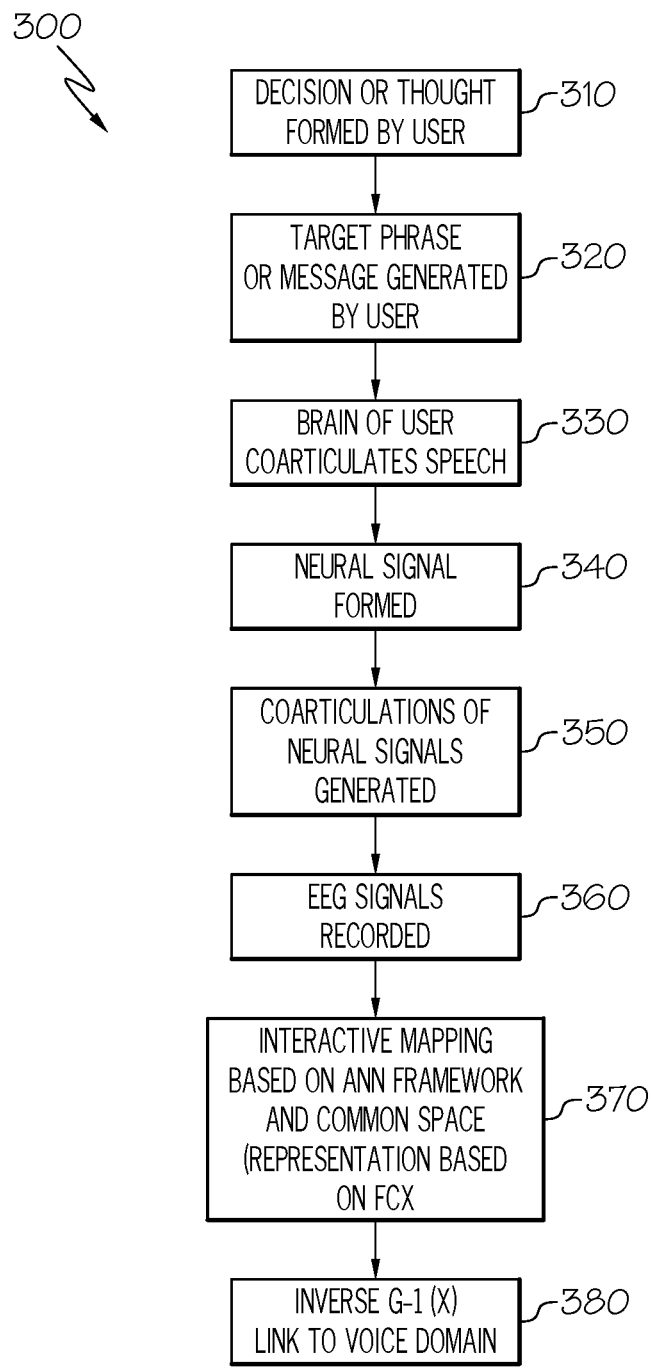
FIG. 3 is a flowchart of an exemplary method of the sub-vocalization speech recovery system in accordance with exemplary embodiments described herein.

FIG. 3 illustrates a flowchart of the sub-vocalization process in accordance with an exemplary embodiment. The flow process of the flowchart 300 follows a representation of speech production by a user. By using a continuous learning or training in a closed loop of an user in the sub-vocalization training process, a sufficient performance level of accuracy of the determined sub-vocalized speech can be achieved by generating a sufficiently large data set of mapped neural activity. The flow process of the flowchart 300 allows for the presence of large amounts of data to be collected from user which is critical to achieving the higher level of accuracy and in turn, enables the ability use of neural networks to perform data driven nonlinear mapping between EEG and voice sub-vocalization. Initially, at task 310, after a decision, notion, or thought is formed by the user. Then at task 320, a target phrase or message is generated by the user. Then, at task 330, the brain of the user coarticulates the speech which consists of sounds assimilated together. At task 340, neural signals from the brain of user are formed and sent to the speech articulators of the user in order to produce the speech or sounds that were formed. At task 350, during the instance of producing speech and sound, brain activity is detected by body sensors related to the coarticulations of neural signals generated for commands of the speech articulators. At task 360, an EEG signal or other type of signal is recorded for use in the continuous to continuous mapping in a feature space. At task 370, an iterative or loop task takes place of continuously mapping all the EEG signals or other types of signals in to a common space or feature space that associates the EEG domain of the EEG signals with produced voice domain from the sub-vocalization of the user. Further, at this stage, no classification of the EEG signals is performed, rather the iterative process of the continuous to continuous mapping forms a signal mapping of an inherent classification by clustering or pattern forming by the continuous to continuous mapped signals in the feature space or target area, for example target area (A). Hence, the sub-vocalization system at task 370 performs a continuous-to-continuous signal mapping from EEG, to audio/speech, through a non-linear regression framework which is designed using ANNs through iterations without requiring a prior knowledge of the relationships. Further, ANN based algorithms are enabled during the continuous-to-continuous mapping for simultaneous training of functions $f$, $g$ and a representation target space defined by common neural activation. In this process flow, at task 370 the function $f$ map EEG/EMG to the common representation space and the function g targets a map of the voice signal to that space. At task 370, to reproduce the subvocalized voice, the process flow will use the mapping function $f$ to map the EEG/EMG signal to the common space and then at task 380 will utilize the inverse of g or an estimation of inverse of function g, $g^{-1}(f)$, to produce the subvocalized voice.

Figure 4:
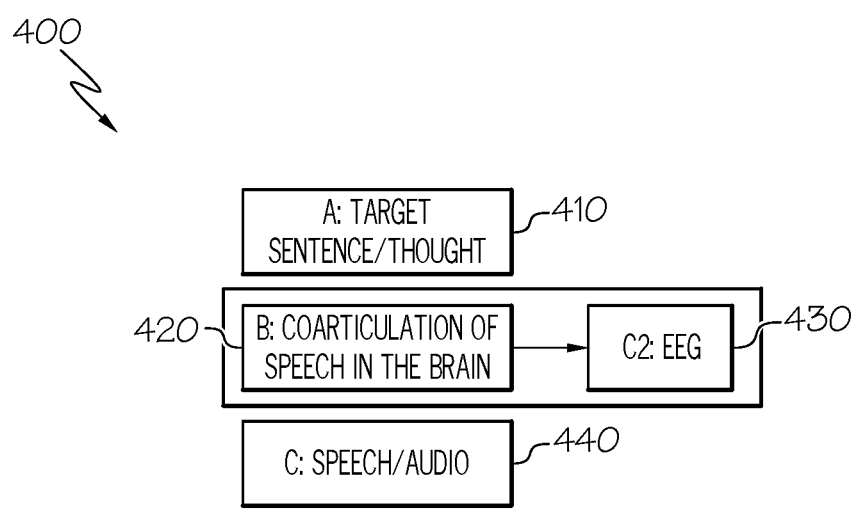
FIG. 4 is a block diagram of a sub-vocalization speech recovery system in accordance with the exemplary embodiments described herein.

FIG. 4 is a diagram of a sub-vocalization speech recovery system in accordance with the exemplary embodiments.

FIG. 4 illustrates the speech generation solution by showing a mapping process from an EEG signal. In this instance, the EEG signal generated is not based on the user intent. In other words, in exemplary embodiment, illustrated in FIG. 4, a mapping of "C2" referenced as 430 at the EEG to "C1" referenced as 440 of the speech and audio determinations is based on the mapping from "C2" referenced a 430 at the EEG to a target sentence or thought at "A" referenced as 410 of a particular word or phoneme classification scheme. In an exemplary embodiment, a continuous-to-continuous mapping of "C2" at 430 of the EEG to "C1" speech and audio is performed by constructing "C2" at 430 of the EEG to "B" at 420 by a coarticulation of speech in the brain to "C1" at 440 of the speech and audio. In instances, the EEG classification may involve imagined or subvocalized vowels or words. For example, in the present instance, a direct mapping of EEG to an audio signal is performed by constructing a common subspace that associates the EEG domain with produced voice domain. A continuous learning in a closed loop of 400, of a human-in-the-loop manner is achieved and a robust and acceptable performance level of accuracy of the determined imagine speech results. Also, because the process allows for the presence of large amounts of data to be collected from individuals, this enables the ability to use neural networks to perform data driven nonlinear mapping between EEG and voice sub-vocalization. Neural networks are not required nor used with this process because in a BCI domain the amount of the collected data would not be sufficient for training.

With continuing reference to FIG. 4, in FIG. 4 a schematic representation of speech production of the user is illustrated. In the speech production mechanism of system 400 after the decision is made by the user, a target phrase/massage may be proposed (for example, may be represented by A at 410). Then, the brain of the user would perform the coarticulation (i.e. assimilation of speech sounds) of the speech as in B at 420 and then in turn sends neural signals for commands to speech articulators to produce speech/audio as in C1 at 440. In an exemplary embodiment, during brain activity related to the coarticulations and neural commands generation for speech articulators, a desired EEG signal may also be recorded in C2 at 430. At this stage, the focus is not on a classification task to infer the proposed user target (A), from EEG signal (C1) for silent speech sub-vocalization but to perform a continuous-to-continuous signal mapping from the EEG at C2 at 430 to the audio/speech C1 at 440 through a non-linear regression framework. The non-linear framework is implemented by using ANNs cycling through iterative cycles without requiring any prior knowledge of the relationships of the data received. Both C1 at 440 and C2 at 430 are byproducts of the same coarticulation activity in B at 420.

With further reference to FIG. 4, in FIG. 4 the use of a target sentence or thought at "A" at 410 of a particular word or phoneme mapping schemer to maximize consistency may be implemented. In an exemplary embodiment, a data collection process which may be standardized may be used and can be based on; for example, how many 1-second samples are taken for each word? e.g. 5 samples per word means 5 seconds of simultaneous EEG and audio recordings etc. A verbal queue may be for a general explanation to the user to provide consistency in the instructions for test subjects during the data collection phase. After initiating the appropriate verbal queue, the system 400 may allow the user a few seconds to stabilize focus on a correct label. Once, the system 400 discerns or observes that the user is sufficiently focused, the system 400 may collect the appropriate number of 1-second data samples from synchronized EEG. The system 400 may simultaneously record data from both the EEG headset and the electrode transmissions every time a character is voiced. A variety of different characters may be assigned to each label representing an sub-vocalization word or phrase.

Figure 5:
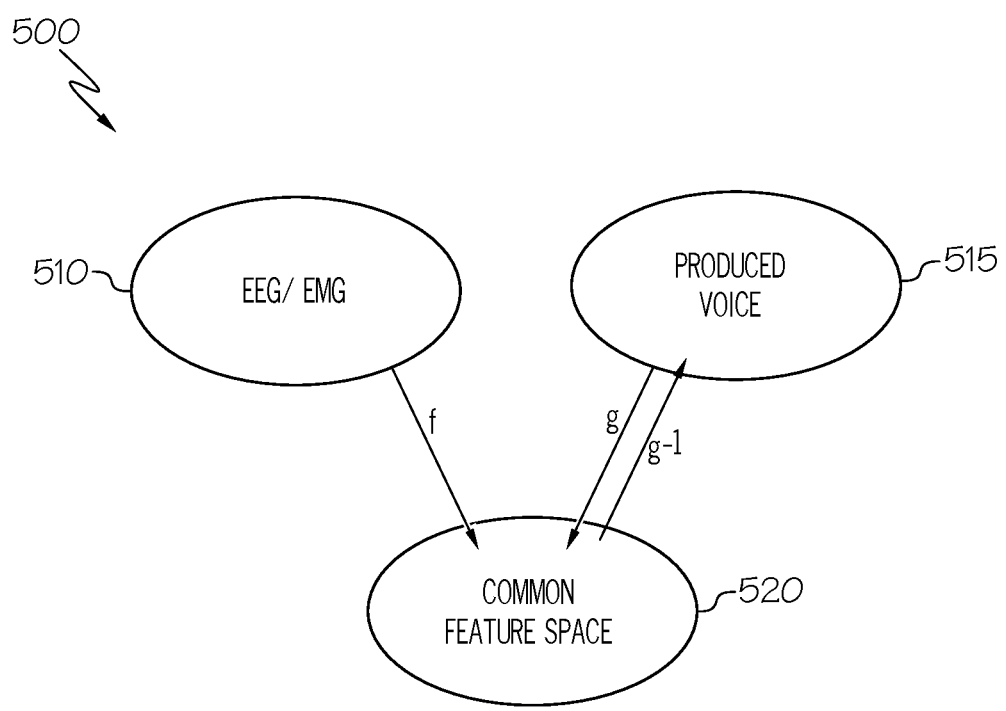
FIG. 5 is a diagram sub-vocalization speech recovery system in accordance with exemplary embodiments described herein.

FIG. 5 is a diagram sub-vocalization speech recovery system in accordance with exemplary embodiments. FIG. 5. illustrates a proposed mapping by system 500 based on various underlying assumptions and a structure proposed for a machine learning algorithm for continuous-to-continuous iterative signal mapping. First, an EEG and or another signal type, e.g. EMG, recording in the system 500 is formed which is relates to neural activations during speech/voice coarticulation or motor command generation/transmission by a user. The recordings at 510 can be considered a byproduct of various neural activations which are related to sub-vocalization and which is aimed to produce the voice at 515. During the training of the system 500, the EEG data is annotated with the produced (or aimed to be produce) sound. In instances, an ANN based algorithms may be used for simultaneously learning or implementation of a set of functions $f$, $g$ and an associated representation space which can be defined by common neural activations at 520. In the system 500, the function $f$ is aimed to map the EEG/EMG at 510 to the common representation space and the function $g$ is targeted to map to the voice signal at 515 to the produced voice space. During the system 500 operation, in order to reproduce the subvocalized voice, the system 500 uses the mapping function $f$ to map the EEG/EMG signal at 510 to the common space and then utilizes the inverse of $g$ or an estimation of inverse of function $g$, $f^{-1}g$, to produce the voice at 515.

With continuing reference to FIG. 5, FIG. 5 illustrates a direct mapping of system 500 of the sub-vocalization voice with vowels or words to the produced voice at 515 in accordance with an exemplary embodiment. That is, there the step of EEG classification is omitted for imagined or subvocalized vowels or words, because a direct mapping of EEG at 510 to audio signal at 515 can be implemented by constructing a common feature space or subspace at 520 which associates the EEG domain of the EEG signal at 510 with produced voice domain of the produced voice at 515. In FIG. 5, the system 500 implements the mapping from EEG/EMG 510 to produced voice $f^{-1}g$ 515 based on signals from the EEG/EMG 510 that are within the common feature space at 520. The common feature space at 520 includes implicitly an extraction as well as a feature clustering and/or a projection in a single step f(x) which enables and defines the common feature space at 520. The common feature space at 520 may be linked to the produced voice at 515 of a particular data set(f) which in turn may be linked to the produced voice at 515.

In an exemplary embodiment, an arbitrary list of features, may be selected the most discriminant for each common feature space at 520. The initial list of common feature space at 520 may be based on complex combinations of power spectra. But generally, this space is an abstract representation space that includes ANN activation function outputs.

In an exemplary embodiment, it may be determined which common feature space at 520 allows for a best discrimination between vowels. For example, the differences between vowels may be found in broad areas at specific frequency bands.

In addition, appropriate processing during the mapping is necessary to standardize the dataset and eliminate inconsistencies that may have skewed results may be implemented in the system 500. The raw data received (i.e. data for body sensors) in instances, can be stripped down to allow for more efficient processing without compromising the integrity or the content of the data.

The recorded EEG signals at 510 may consist of a large number of simultaneous fired neurons. In order to select a suitable mapping algorithm, it is required to find any or all of the sources, properties, and features of the data. Four most common groups of features are time-domain features (TDF), frequency-domain features (FDF), wavelet features (WF), and cepstral features (CF). The sub-vocalization system needs enough data to describe the different categories and find the proper class for a newcomer signal. Depending on feature vector dimensionality, the required data will be increased exponentially. For a good performance, the training samples may have more than at least five times of data compared to data of the feature vector dimensionality required.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate the interchangeability of hardware and software, various illustrative components, blocks, modules, circuits, and steps have been described above generally in terms of their functionality.

Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a controller or processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for sub-vocalization, the method comprising:
performing, by a processor that executes instructions contained in a non-transitory computer read-able medium, a continuous-to-continuous mapping of neural signal data received from one or more body sensors connected to a user, wherein the one or more body sensors monitor at least neural activities of the user of a sub-vocalized voice at a sensory level and sends the neural signal data to the processor;
receiving, by the processor, the neural signal data in an iterative closed loop for training the processor wherein the training enables generating a sufficiently large data set in the neural signal domain from the neural signal data to link to a produced voice domain;
constructing a common feature space, by the processor, which associates the neural signal domain with the produced voice domain for producing audio communications, wherein the common feature space implicitly extracts features related to audio communications using the sufficiently large data set by the common feature space for linking neural signal domain data to the produced voice data without requiring any prior feature classification of the received neural signal data;

modeling, by artificial neural networks (ANN), the continuous-to-continuous mapping of neural signal data received from the one or more body sensors connected to the user;

learning, by the processor, by iterations of the closed loop training of the processor a mapping of the common feature space for a set of common neural signal domain activity and, by applying a set of ANN based algorithms of the ANN while simultaneously modeling the common feature space;

mapping, by a first function, the neural signal domain, and targeting, by a second function, the mapping of the first function to the produced voice domain to reproduce the subvocalized voice; and using a f(x) by the first function for mapping to the common feature space, and using an inverse $G^{-1}(x)$ by the second function for targeting to the produced voice domain.

2. The method of claim 1, further comprising:

monitoring, by the one or more body sensors, neural domain data of sub-vocalized voice of a set of neural signals at least comprising: electroencephalography (EEG), electromyography (EMG), Electroencephalography (EGG) and Functional Near-Infrared Spectroscopy (FNIRS) signals.

3. The method of claim 1, wherein the mapping performed is agnostic as to an intent of the user or monitoring of neural activities.

4. A sub-vocalization system of imagined speech, comprising:

a plurality of body sensors;

a processor, that executes instructions contained in a non-transitory computer read-able medium, to perform a continuous-to-continuous mapping of neural signal data received from one or more body sensors from the plurality of body sensors connected to a user, wherein the one or more body sensors monitor at least neural activities of the user of a sub-vocalized voice at a sensory level and sends the neural signal data to the processor; and an artificial neural network (ANN) to model the continuous-to-continuous mapping of neural signal data received from the one or more body sensors connected to the user, the processor configured to:

process a set of neural signal data received from the one or more body sensors in an iterative closed loop for training the processor, wherein the training generates a sufficiently large data set in the neural signal domain from the neural signal data to link to a produced voice domain;

construct a common feature space, which associates the neural signal domain with the produced voice domain to produce audio communications, wherein the common feature space implicitly extracts features related to audio communications, using the sufficiently large data set, by the common feature space to link neural signal domain data to the produced voice data without requiring any prior feature classification of the received neural signal data;

learn, using a data learning, by performing iterations of the closed loop training of the processor of a mapping of the common feature space for a set of common neural signal domain activity, and by applying a set of ANN based algorithms of the ANN while performing a data modeling of the common feature space; and perform a first function to map the neural signal domain, and a second function to target the map of the first function to the produced voice domain to reproduce the subvocalized voice wherein a f(x) is used by the first function to map to the common feature space, and an inverse $G-1(x)$ is used by the second function for targeting to the produced voice domain.

5. The system of claim 4, further comprising:

the set of body sensors configured to:

monitor a set of a plurality of neural signals monitored for recording neural domain data of sub-vocalized voice, the set of neural signals at least comprises: electroencephalography (EEG), electromyography (EMG), Electroencephalography (EGG) and Functional Near-Infrared Spectroscopy (FNIRS) signals.

6. The system of claim 4, wherein the mapping by the processor is agnostic as to an intent of the user or type of neural activities.

* * * * *